United States Patent
Gocho et al.

(10) Patent No.: US 9,426,374 B2
(45) Date of Patent: Aug. 23, 2016

(54) IMAGE PICKUP APPARATUS

(71) Applicant: OLYMPUS CORPORATION, Tokyo (JP)

(72) Inventors: Masanori Gocho, Tokyo (JP); Masaki Kondo, Tokyo (JP); Ken Fukumoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 14/882,187

(22) Filed: Oct. 13, 2015

(65) Prior Publication Data

US 2016/0037079 A1 Feb. 4, 2016

Related U.S. Application Data

(63) Continuation of application No. PCT/JP2014/063623, filed on May 22, 2014.

(30) Foreign Application Priority Data

Jul. 29, 2013 (JP) ................................ 2013-156872

(51) Int. Cl.
*H04N 3/06* (2006.01)
*H04N 5/262* (2006.01)
(Continued)

(52) U.S. Cl.
CPC ....... *H04N 5/23296* (2013.01); *A61B 1/00188* (2013.01); *A61B 1/045* (2013.01);
(Continued)

(58) Field of Classification Search
CPC ........ G02B 7/102; G02B 7/282; G02B 7/04; G02B 15/00; G03B 13/18; G03B 13/30; G03B 2205/0046; G05B 2219/45178
USPC ....... 348/202, 335, 345, 347, 240.3, 240.99, 348/65–76; 396/86, 87
See application file for complete search history.

(56) References Cited

U.S. PATENT DOCUMENTS 4,903,134 A * 2/1990 Murashima ........ H04N 5/23212 348/347
5,574,502 A * 11/1996 Haruki ............... H04N 5/23212 348/347

(Continued)

FOREIGN PATENT DOCUMENTS

JP H04-331907 A 11/1992
JP H08-248292 A 9/1996

(Continued)

OTHER PUBLICATIONS

Aug. 26, 2014 Written Opinion issued in International Patent Application No. PCT/JP2014/063623.

(Continued)

*Primary Examiner* — Chia-Wei A Chen
(74) *Attorney, Agent, or Firm* — Oliff PLC (57) ABSTRACT

An image pickup apparatus includes: an optics system that forms an optical image of a subject on an imaging surface; a variable magnification lens that is part of the optics system, that is provided to be movable in a direction of an optical axis of the optics system, and that enlarges or reduces the optical image formed on the imaging surface in association with a movement of the variable magnification lens; a position detection unit that detects a position of the variable magnification lens in the direction of the optical axis; a storage unit that stores output characteristic information about a characteristic of an output of the position detection unit according to a position of the variable magnification lens in the direction of the optical axis; and a driving control unit that performs a control for moving the variable magnification lens on the basis of the output characteristic information.

3 Claims, 6 Drawing Sheets

(51) Int. Cl.
  H04N 5/225    (2006.01)
  G02B 13/16    (2006.01)
  G03B 13/00    (2006.01)
  H04N 5/232    (2006.01)
  G03B 17/00    (2006.01)
  A61B 1/00     (2006.01)
  A61B 1/045    (2006.01)
  G02B 23/24    (2006.01)
  A61B 1/05     (2006.01)

(52) U.S. Cl.
  CPC ........ *G02B23/2438* (2013.01); *H04N 5/2254* (2013.01); *A61B 1/05* (2013.01); *H04N 2005/2255* (2013.01)

(56) References Cited

U.S. PATENT DOCUMENTS

| | | | | |
|---|---|---|---|---|
| 5,860,032 | A * | 1/1999 | Iwane | G02B 7/28 396/125 |
| 7,738,027 | B2 * | 6/2010 | Cho | H04N 5/232 348/345 |
| 2001/0012074 | A1 * | 8/2001 | Ohkawara | H04N 5/23212 348/240.3 |
| 2004/0027687 | A1 * | 2/2004 | Bittner | G02B 7/102 359/694 |
| 2006/0066745 | A1 * | 3/2006 | Lee | G02B 7/102 348/357 |
| 2008/0084497 | A1 * | 4/2008 | Sasaki | G02B 7/282 348/353 |
| 2009/0161232 | A1 * | 6/2009 | Iwasaki | G02B 7/102 359/697 |
| 2009/0244325 | A1 * | 10/2009 | Honjo | G02B 7/102 348/231.99 |
| 2012/0120303 | A1 * | 5/2012 | Yamanaka | G02B 7/102 348/347 |
| 2013/0222926 | A1 * | 8/2013 | Kawada | G03B 3/10 359/696 |
| 2014/0198246 | A1 * | 7/2014 | Ono | G02B 7/282 348/353 |
| 2015/0146079 | A1 * | 5/2015 | Kim | H04N 5/23293 348/345 |

FOREIGN PATENT DOCUMENTS

| | | |
|---|---|---|
| JP | H09-187040 A | 7/1997 |
| JP | 2010-282073 A | 12/2010 |
| JP | 2011-015883 A | 1/2011 |
| JP | 2011-098051 A | 5/2011 |

OTHER PUBLICATIONS

Aug. 26, 2014 Search Report issued in International Patent Application No. PCT/JP2014/063623.
Jan. 27, 2015 Office Action issued in Japanese Patent Application No. 2014-555020.
Mar. 31, 2015 Office Action issued in Japanese Patent Application No. 2014-555020.

* cited by examiner

IMAGE PICKUP APPARATUS

CROSS-REFERENCE TO RELATED APPLICATIONS

This application is based upon and claims the benefit of priority of the prior Japanese Patent Application No. 2013-156872, filed on Jul. 29, 2013, the entire contents of which are incorporated herein by reference.

This is a Continuation Application of PCT Application No. PCT/JP2014/063623, filed on May 22, 2014, which was not published under PCT Article 21(2) in English.

FIELD

The present invention relates to an image pickup apparatus having a zoom mechanism.

BACKGROUND

Conventionally, an image pickup apparatuses provided with a zoom mechanism is presented.

For example, in an endoscope field, such an image pickup apparatus is provided in an endoscope system. In this case, a zoom mechanism and the like of the image pickup apparatus are provided within a small space called a tip portion of an endoscope in the endoscope system. Accordingly, an image pickup apparatus provided in the endoscope system sometimes includes, as a zoom mechanism, a zoom mechanism using a VCM (Voice Coil Motor) that is advantageous for downsizing. With such a zoom mechanism, the VCM moves a zoom lens so that an optical image formed on an imaging surface is enlarged or reduced.

As other image pickup apparatuses that are included in an endoscope system and have a zoom mechanism, image pickup apparatuses that are disclosed, for example, by Japanese Laid-open Patent Publication No. 2011-98051, Japanese Laid-open Patent Publication No. 2010-282073 and Japanese Laid-open Patent Publication No. 2011-15883, and that include a zoom mechanism are known.

In the above described image pickup apparatus having the zoom mechanism using the VCM, the position of the zoom lens is not fixedly retained by the VCM. Therefore, a feedback control (servo control) for detecting the position of the zoom lens and for moving the zoom lens to a target position on the basis of a result of the detection is always performed. Here, the position of the zoom lens is detected by a position detection mechanism. Similarly to the zoom mechanism, the position detection mechanism is provided within a small space called a tip portion of an endoscope. Therefore, a position detection mechanism of a small size is used.

SUMMARY

One aspect of the present invention provides an image pickup apparatus including: an image pickup optics system that forms an optical image of a subject on an imaging surface; a variable magnification lens that is part of the image pickup optics system, that is provided to be movable in a direction of an optical axis of the image pickup optics system, and that enlarges or reduces the optical image formed on the imaging surface in association with a movement of the variable magnification lens; a position detection unit that detects a position of the variable magnification lens in the direction of the optical axis; a storage unit that stores, as output characteristic information about a characteristic of an output of the position detection unit according to a position of the variable magnification lens in the direction of the optical axis, information including a wide-angle-end output value, which is an output value of the position detection unit when the variable magnification lens is made to touch a wide-angle end, a telephoto-end output value, which is an output value of the position detection unit when the variable magnification lens is made to touch a telephoto end, and a slope of a linear line obtained when the characteristic of the output of the position detection unit according to the position of the variable magnification lens in the direction of the optical axis is linearly approximated in each of a plurality of small sections into which a movement section from the wide-angle end to the telephoto end of the variable magnification lens is partitioned; and a driving control unit that performs a control for moving the variable magnification lens on the basis of the output characteristic information. In this apparatus, the driving control unit performs the control for moving the variable magnification lens on the basis of the output characteristic information so that a result of a multiplication between an inverse number of a slope of a linear line corresponding to a small section to which the current position of the variable magnification lens belongs and the amount of an output change of the position detection unit per unit time can become constant.

DESCRIPTION OF EMBODIMENTS

Embodiments according to the present invention are described below with reference to the drawings.

<First Embodiment>

Figure 1:
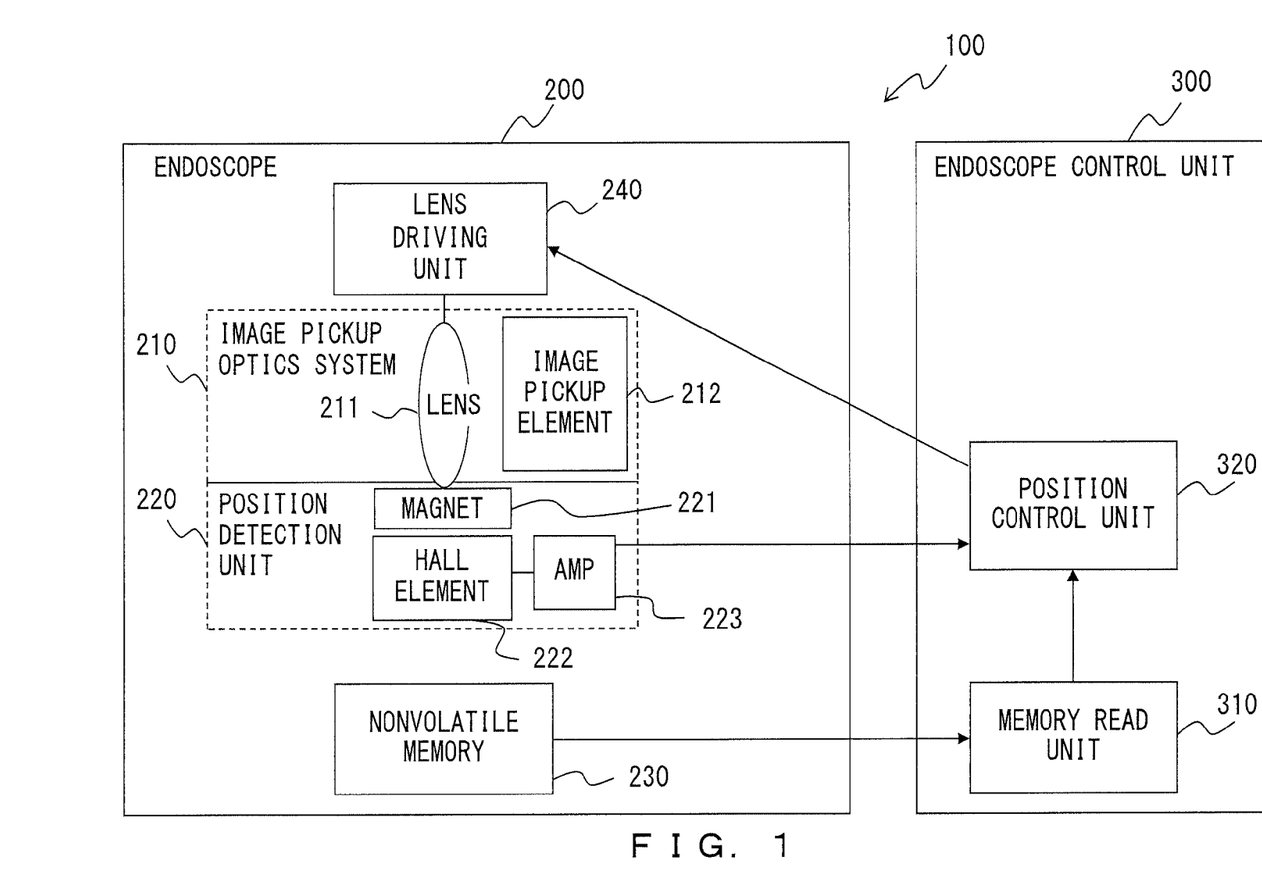
FIG. 1 illustrates a configuration example of an endoscope system including an image pickup apparatus.

FIG. 1 illustrates a configuration example of an endoscope system including an image pickup apparatus according to a first embodiment of the present invention.

As illustrated in FIG. 1, an endoscope system 100 is configured by including an endoscope 200 and an endoscope control unit 300 so that signals can be transmitted and received between the endoscope 200 and the endoscope control unit 300.

The endoscope 200 includes an image pickup optics system 210, a position detection unit 220, a nonvolatile memory 230, and a lens driving unit 240.

The image pickup optics system 210 forms an optical image of a subject on an imaging surface of an image pickup element 212, and includes a zoom lens 211 and the image pickup element 212.

The zoom lens 211 is a variable magnification lens that is provided to be movable in a direction of an optical axis of the image pickup optics system 210, and that enlarges or reduces the optical image formed on the imaging surface of the image pickup element 212 by means of a movement of the zoom lens 211.

The image pickup element 212 is an image pickup element having a color filter such as a Bayer arrangement, and picks up the optical image formed on the imaging surface. An output signal of the image pickup element 212 is output to the endoscope control unit 300, and is made visible, for example, on a display unit as an image after the endoscope control unit 300 executes a specified image process and the like for the signal.

The position detection unit 220 detects the position of the zoom lens 211 in the direction of the optical axis of the image pickup optics system 210, and includes a magnet 221, a Hall element 222, and an AMP (Amplifier) 223.

The magnet 221 is secured to part of the zoom lens 211 so that it can move along with the zoom lens 211.

The Hall element 222 detects a magnetic field by using the Hall effect, and outputs an analog signal proportional to the intensity of the magnetic field. Here, the Hall element 222 detects the magnetic field according to a positional relationship with the magnet 221, and outputs an analog signal proportional to the intensity of the magnetic field.

The AMP 223 is a circuit that amplifies and outputs the output signal of the Hall element 222. The output signal of the AMP 223 is output to the position control unit 320 of the endoscope control unit 300.

The nonvolatile memory 230 is, for example, an EEPROM (Electrically Erasable Programmable Read-Only Memory), and stores output characteristic information of a characteristic of the output of the position detection unit 220 according to the position of the zoom lens 211 in the direction of the optical axis of the image pickup optics system 210.

The lens driving unit 240 is a VCM, and moves the zoom lens 211 in the direction of the optical axis of the image pickup optics system 210 in accordance with a driving signal from the position control unit 320 of the endoscope control unit 300.

In the endoscope 200, the image pickup optics system 210, the position detection unit 220, and the lens driving unit 240 are provided within the tip portion of the endoscope 200.

The endoscope control unit 300 controls operations of the entire endoscope system 100, and includes a memory read unit 310 and the position control unit (one example of the driving control unit) 320.

The memory read unit 310 reads the output characteristic information from the nonvolatile memory 230 of the endoscope 200, and outputs the read information to the position control unit 320.

The position control unit 320 performs a control for moving the zoom lens 211 in the direction of the optical axis of the image pickup optics system 210 on the basis of the output characteristic information from the memory read unit 310. More specifically, the position control unit 320 outputs, to the lens driving unit 240, the driving signal for moving the zoom lens 211 in the direction of the optical axis of the image pickup optics system 210 on the basis of the output characteristic information from the memory read unit 310 and the output signal of the position detection unit 220. The position control unit 320 controls the move (position) of the zoom lens 211 by performing the feedback control (servo control). Actually, the position control unit 320 outputs, to the lens driving unit 240, the driving signal for moving the zoom lens 211 to a target position on the basis of the output characteristic information and the output signal of the position detection unit 220 every unit time (at specified time intervals).

The endoscope system 100 also includes an operation unit or the like that accepts various types of instructions from a user, although this unit is not illustrated.

In the endoscope system 100 having such a configuration, the output characteristic information stored in the nonvolatile memory 230 of the endoscope 200 is stored prior to factory shipment. More specifically, for example, at a point in time when the endoscope 200 has been assembled, a wide-angle-end output value, which is an output value of the position detection unit 220 when the zoom lens 211 is made to touch the wide-angle end, and a telephoto-end output value, which is an output value of the position detection unit 220 when the zoom lens 211 is made to touch the telephoto end, are obtained. Then, the output characteristic information including both of the output values is stored in the nonvolatile memory 230. Note that the wide-angle end is a position on the widest-angle side in a movable range of the zoom lens 211, and the telephoto end is a position on the most telephoto side in the movable range of the zoom lens 211.

Zoom operations performed in the endoscope system 100 including the image pickup apparatus according to this embodiment are described next.

The endoscope system 100 moves the zoom lens 211 in accordance with a zoom instruction upon acceptance of the zoom instruction from a user. Note that the zoom instruction is accepted by pressing a wide-angle zoom button or a telephoto zoom button that is included in the operation unit, not illustrated, of the endoscope system 100. Namely, a wide-angle zoom instruction is issued with a press of the wide-angle zoom button, or a telephoto zoom instruction is issued with a press of the telephoto zoom button.

The endoscope system 100 moves the zoom lens 211 to the side of the wide-angle end while the wide-angle zoom button is being pressed (the wide-angle zoom instruction is continuously issued), or moves the zoom lens 211 to the side of the telephoto end while the telephoto zoom button is being pressed (the telephoto zoom instruction is continuously issued). Moreover, in the endoscope system 100, when the pressing of the wide-angle zoom button or the telephoto zoom button is released, the zoom lens 211 is retained at the position of the zoom lens 211 remaining at the time point when the pressing of the button is released.

More specifically, such zoom operations are performed as follows.

The zoom operations are performed in a way such that the position control unit 320 outputs, to the lens driving unit 240, a driving signal for moving the zoom lens 211 on the basis of a characteristic linear line defined with the output characteristic information that the memory read unit 310 reads from the nonvolatile memory 230 and the output signal of the position detection unit 220 (the AMP 223). Note that the characteristic linear line defined with the output characteristic information is a linear line that is plotted in a coordinate system (for example, see the coordinate system illustrated in FIG. 2 to be described later) when the position of the zoom lens 211 and the output of the position detection unit 220 are taken respectively as horizontal and vertical axes, and that links a point of the wide-angle-end output value and a point of the telephoto-end output value. The wide-angle-end output value and the telephoto-end output value are included in the output characteristic information as described above. With such a characteristic linear line, a relationship between the position of the zoom lens 211 and the output of the position detection unit 220 in the endoscope 200 is defined.

For example, while the wide-angle zoom button or the telephoto zoom button is being pressed, the position control unit 320 outputs, to the lens driving unit 240, a driving signal for moving the zoom lens 211 at a constant velocity, on the basis of the characteristic linear line and the output signal of the position detection unit 220. Moreover, for example, when the pressing of the wide-angle zoom button or the telephoto zoom button is released, the position control unit 320 outputs, to the lens driving unit 240, a driving signal for retaining the zoom lens 211 at the position of the zoom lens 211 remaining at the time point when the pressing of the button is released, on the basis of the characteristic linear line and the output signal of the position detection unit 220.

As described above, with the endoscope system 100 including the image pickup apparatus according to this embodiment, a characteristic linear line used when a zoom operation is performed is defined with a wide-angle-end output value and a telephoto-end output value that are obtained in the endoscope 200 at a time point when the endoscope 200 has been assembled. Therefore, manufacturing variations in the position detection unit 220 (the magnet 221 and the Hall element 222) and the like of the endoscope 200 are taken into account. Accordingly, the position of the zoom lens can be accurately controlled in the zoom operation.

<Second Embodiment>

An endoscope system including an image pickup apparatus according to a second embodiment of the present invention is implemented by further improving the endoscope system including the image pickup apparatus according to the first embodiment. This embodiment is described by attaching the same reference numerals as those of the first embodiment to the same components as those described in the first embodiment.

Figure 2:
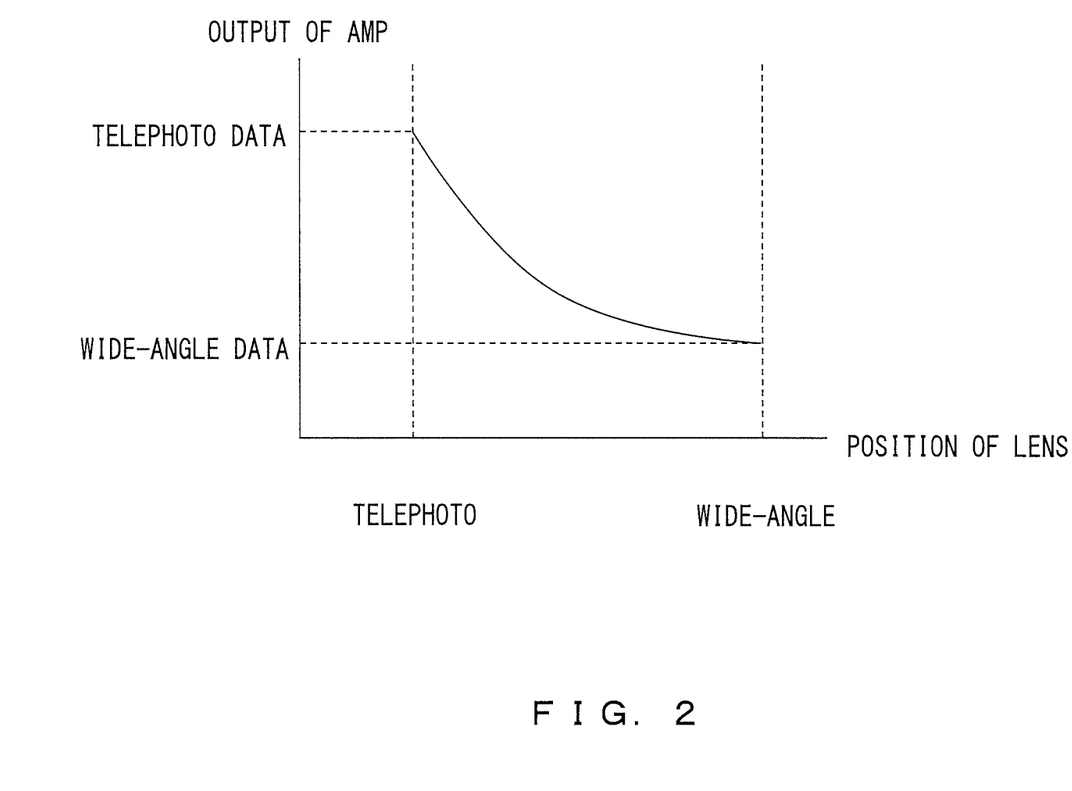
FIG. 2 illustrates an example where a relationship between a position of a zoom lens and an output of a position detection unit (AMP) is not linear.

When the tip portion of the endoscope 200 is further downsized, the space within the tip portion becomes smaller, so that the magnet 221 and the Hall element 222 that are provided within the tip portion become closer. In such a case, the relationship between the position of the zoom lens 211 and the output of the position detection unit 220 (the AMP 223) does not become linear, for example, as illustrated in FIG. 2, due to a relationship between a magnet and a magnetic field, leading to a possibility that the position of the zoom lens cannot be accurately controlled in the zoom operation.

For this reason, in the endoscope system 100 including the image pickup apparatus according to this embodiment, the output characteristic information stored in the nonvolatile memory 230 and the zoom operation are different from those of the endoscope system 100 including the image pickup apparatus according to the first embodiment, as will be described later, so that the position of the zoom lens can be more accurately controlled in the above described case.

In the endoscope system 100 including the image pickup apparatus according to this embodiment, the output characteristic information stored in the nonvolatile memory 230 includes the output value of the position detection unit 220 (the AMP 223) at each partitioned position (a position interposed between adjacent small sections), and a slope of a characteristic linear line in each of the small sections when the movement section from the wide-angle end to the telephoto end of the zoom lens 211 is partitioned into a plurality of small sections, in addition to the wide-angle-end output value and the telephoto-end output value. The slope of the characteristic linear line in each of the small sections is a slope of a linear line obtained when the relationship between the position of the zoom lens 211 and the output of the position detection unit 220 (the AMP 223) in each of the small sections is linearly approximated.

Figure 3:
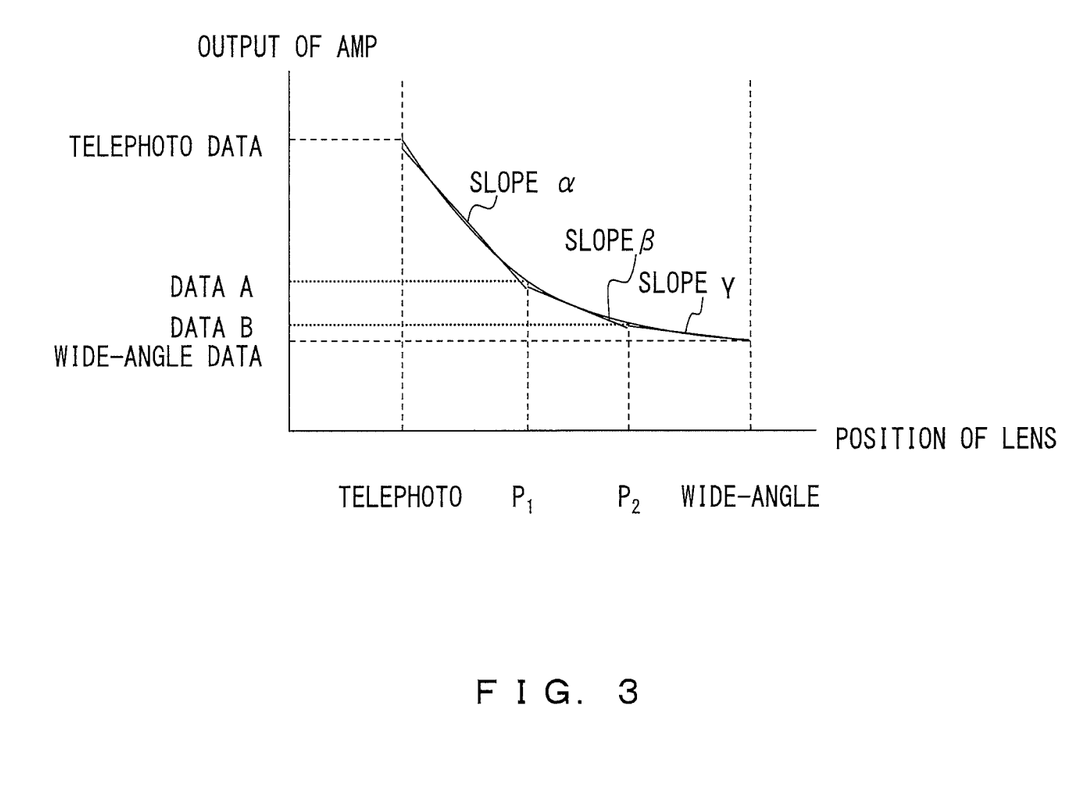
FIG. 3 is an explanatory diagram of an example where a movement section from a wide-angle end to a telephoto end of the zoom lens is partitioned into three small sections.

In this embodiment, it is assumed that the movement section from the wide-angle end (WIDE-ANGLE) to the telephoto end (TELEPHOTO) of the zoom lens 211 is partitioned into three small sections as illustrated in FIG. 3. It is also assumed that the output characteristic information further includes output values A (data A) and B (data B) of the position detection unit 220 at each of partitioned positions P1 and P2, and a slope $\alpha$, $\beta$ and $\gamma$ of a characteristic linear line in each of the small sections in addition to the wide-angle-end output value and the telephoto-end output value. $\alpha$ indicates the slope of the linear line when the relationship between the position of the zoom lens 211 and the output of the position detection unit 220 is linearly approximated in the small section from the telephoto end to P1. $\beta$ indicates the slope of the linear line when the relationship between the position of the zoom lens 211 and the output of the position detection unit 220 is linearly approximated in the small section from P1 to P2. $\gamma$ indicates the slope of the linear line when the relationship between the position of the zoom lens 211 and the output of the position detection unit 220 is linearly approximated in the small section from P2 to the wide-angle end.

Similarly to the first embodiment, the output characteristic information including these items of data is stored in the nonvolatile memory 230 prior to factory shipment. More specifically, for example, at a time point when the endoscope 200 has been assembled, the relationship (for example, see FIG. 2) between the position of the zoom lens 211 and the output of the position detection unit 220 (the AMP 223) is initially obtained in the endoscope 200. Additionally, the wide-angle-end output value, the telephoto-end output value, the data A, and the data B, $\alpha$, $\beta$, and $\gamma$ are obtained on the basis of the relationship. Then, the output characteristic information including these items of data is stored in the nonvolatile memory 230.

In the endoscope system 100 including the image pickup apparatus according to this embodiment, the zoom operations are performed as follows by using such output characteristic information.

The zoom operations are performed in such a way that the position control unit 320 outputs, to the lens driving unit 240, a driving signal for moving the zoom lens 211 on the basis of the output characteristic information that the memory read unit 310 reads from the nonvolatile memory 230 and the output signal of the position detection unit 220 (the AMP 223).

For example, while the wide-angle zoom button or the telephoto zoom button is being pressed, the position control unit 320 outputs, to the lens driving unit 240, a driving signal for moving the zoom lens 211 at a constant velocity on the basis of the output characteristic information and the output signal of the position detection unit 220. More specifically, the position control unit 320 outputs, to the lens driving unit 240, the driving signal for moving the zoom lens 211 on the basis of the output characteristic information and the output signal of the position detection unit 220 so that a result of a multiplication between an inverse number of the slope of a linear line corresponding to a small section to which the current position of the zoom lens 211 belongs and the amount of an output change of the position detection unit 220 per unit time can become constant. For example, when the small section to which the current position of the zoom lens 211 belongs is the small section from the telephoto end to P1, the position control unit 320 outputs, to the lens driving unit 240, the driving signal for moving the zoom lens 211 so that the result of the multiplication between (1/α) and the amount of the output change of the position detection unit 220 per unit time can become C (constant value). Alternatively, when the small section to which the current position of the zoom lens 211 belongs is the small section from P1 to P2, the position control unit 320 outputs, to the lens driving unit 240, the driving signal for moving the zoom lens 211 so that the result of the multiplication between (1/β) and the amount of the output change of the position detection unit 220 per unit time can become C (the same value as the above described C). Further alternatively, when the small section to which the current position of the zoom lens 211 belongs is the small section from P2 to the wide-angle end, the position control unit 320 outputs, to the lens driving unit 240, the driving signal for moving the zoom lens 211 so that the result of the multiplication between (1/γ) and the amount of the output change of the position detection unit 220 per unit time can become C (the same value as the above described C). With such operations, the moving velocity of the zoom lens 211 becomes constant with a continuous pressing of the wide-angle zoom button or the telephoto zoom button even though the zoom lens 211 moves, for example, from one small section to another. Therefore, the operability is not deteriorated.

Additionally, for example, when the pressing of the wide-angle zoom button or the telephoto zoom button is released, the position control unit 320 outputs, to the lens driving unit 240, a driving signal for retaining the zoom lens 211 at the position of the zoom lens 211 remaining at a time point when the pressing of the button is released, on the basis of the output characteristic information and the output signal of the position detection unit 220. More specifically, the position control unit 320 outputs, to the lens driving unit 240, the driving signal for retaining the zoom lens 211 at the position of the zoom lens 211 remaining at the time point when the pressing of the button is released, on the basis of the slope of a linear line corresponding to a small section to which the current position of the zoom lens 211 belongs and the output signal of the position detection unit 220. For example, when the small section to which the current position of the zoom lens 211 belongs is the small section from the telephoto end to P1, the position control unit 320 outputs, to the lens driving unit 240, the driving signal for retaining the zoom lens 211 at the position of the zoom lens 211 remaining at the time point when the pressing of the button is released, on the basis of the slope α of the corresponding linear line and the output signal of the position detection unit 220. Alternatively, when the small section to which the current position of the zoom lens 211 belongs is the small section from P1 to P2, the position control unit 320 outputs, to the lens driving unit 240, the driving signal for retaining the zoom lens 211 at the position of the zoom lens 211 remaining at the time point when the pressing of the button is released, on the basis of the slope β of the corresponding linear line and the output signal of the position detection unit 220. Further alternatively, when the small section to which the current position of the zoom lens 211 belongs is the small section from P2 to the wide-angle end, the position control unit 320 outputs, to the lens driving unit 240, the driving signal for retaining the zoom lens 211 at the position of the zoom lens 211 remaining at the time point when the pressing of the button is released, on the basis of the slope γ of the corresponding linear line and the output signal of the position detection unit 220.

As described above, with the endoscope system 100 including the image pickup apparatus according to this embodiment, even though the relationship between the position of the zoom lens 211 and the output of the position detection unit 220 is not linear (for example, see FIG. 2), it is approximated with a plurality of linear lines (for example, see FIG. 3), and a zoom operation is performed by using data of a corresponding approximated linear line at each time. Moreover, also in the endoscope system 100 including the image pickup apparatus according to this embodiment, data included in the output characteristic information used when the zoom operation is performed is obtained in the endoscope 200 at a time point when the endoscope 200 has been assembled. Therefore, manufacturing variations in the position detection unit 220 (the magnet 221 and the Hall element 222) and the like of the endoscope 200 are taken into account. Accordingly, the position of the zoom lens can be accurately controlled in the zoom operation. Moreover, the moving velocity of the zoom lens 211 becomes constant while the wide-angle zoom button or the telephoto zoom button is being pressed, whereby the operability is not deteriorated.

This embodiment refers to the example where the movement section from the wide-angle end to the telephoto end of the zoom lens 211 is partitioned into the three small sections as illustrated in FIG. 3. However, the number of partitioned small sections is not limited to three. The movement section may be partitioned into a plurality of small sections other than three.

The first and the second embodiments have been described up to this point. However, the endoscope system 100 including the image pickup apparatus according to each of the embodiments can be variously modified.

For example, in the endoscope system 100 including the image pickup apparatus according to each of the embodiments, each time the system is started up (each time the image pickup apparatus is powered on), the position control unit 320 performs a control for moving the zoom lens 211 from the wide-angle end to the telephoto end, and the endoscope control unit (here, the endoscope control unit is also one example of an obtainment unit and a determination unit) 300 obtains the wide-angle-end output value and the telephoto-end output value from the position detection unit 220 at that time, and determines whether the position detection unit 220 and/or the position control unit 320 is either normal or abnormal, on the basis of the obtained wide-angle-end output value and telephoto-end output value and a wide-angle-end output value and a telephoto-end output value that are included in the output characteristic information stored in the nonvolatile memory 230. When the endoscope control unit 300 determines that the position detection unit 220 and/or the position control unit 320 is abnormal as a result of the determination, it prohibits the zoom operation, and may notify a user that the position detection unit 220 and/or the position control unit 320 is abnormal, for example, by making the result of the determination visible on a display unit not illustrated. For example, when the wide-angle-end output value obtained from the position detection unit 220 is lower than 50 percent of the wide-angle-end output value included in the output characteristic information, and/or when the telephoto-end output value obtained from the position detection unit 220 is lower than 50 percent of the telephoto-end output value included in the output characteristic information, the endoscope control unit 300 determines that the position detection unit 220 and/or the position control unit 320 is abnormal. Such operations are performed each time the system is started up, whereby a problem, caused by a temperature change, an aging deterioration or the like, of the position detection unit 220 (such as the Hall element 222) and/or the position control unit 320 can be detected. In the endoscope system 100 including the image pickup apparatus according to the first embodiment, a characteristic linear line defined with a wide-angle-end output value and a telephoto-end output value that are obtained when the system is started up may be used as a characteristic linear line used for a zoom operation when the endoscope control unit 300 determines that the position detection unit 220 and/or the position control unit 320 is normal.

Figure 4:
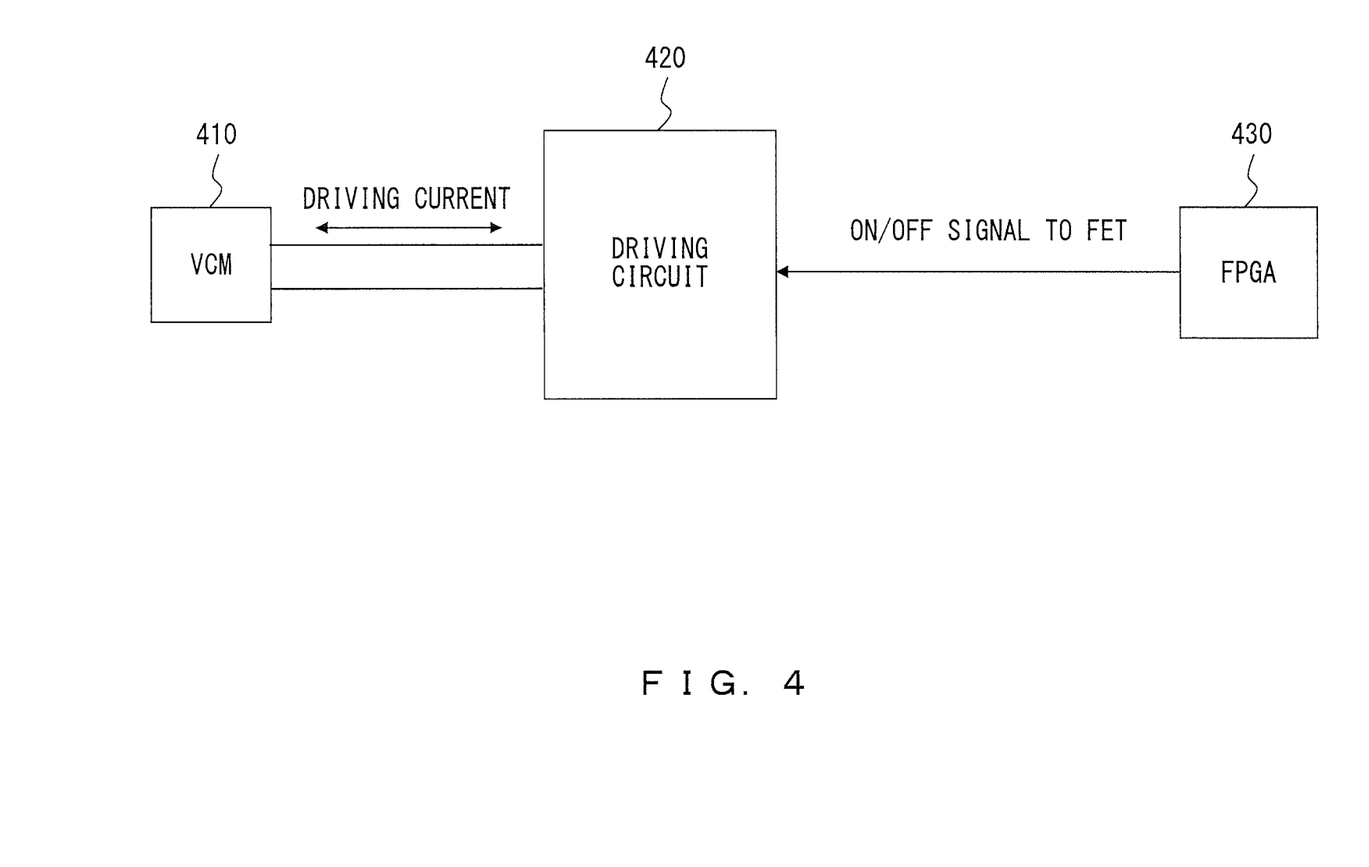
FIG. 4 illustrates a configuration example of a lens driving unit and a position control unit.
Figure 5:
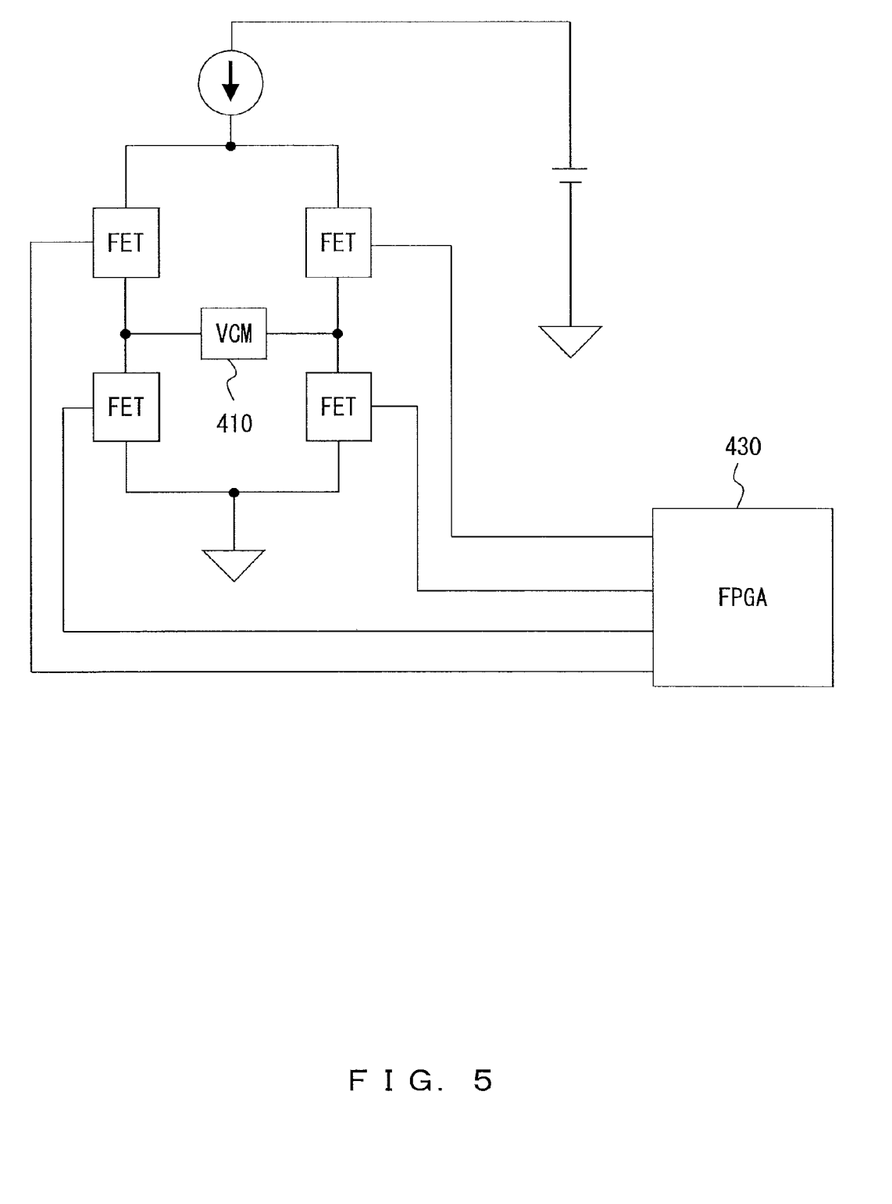
FIG. 5 illustrates a configuration example of a VCM driving circuit.
Figure 6:
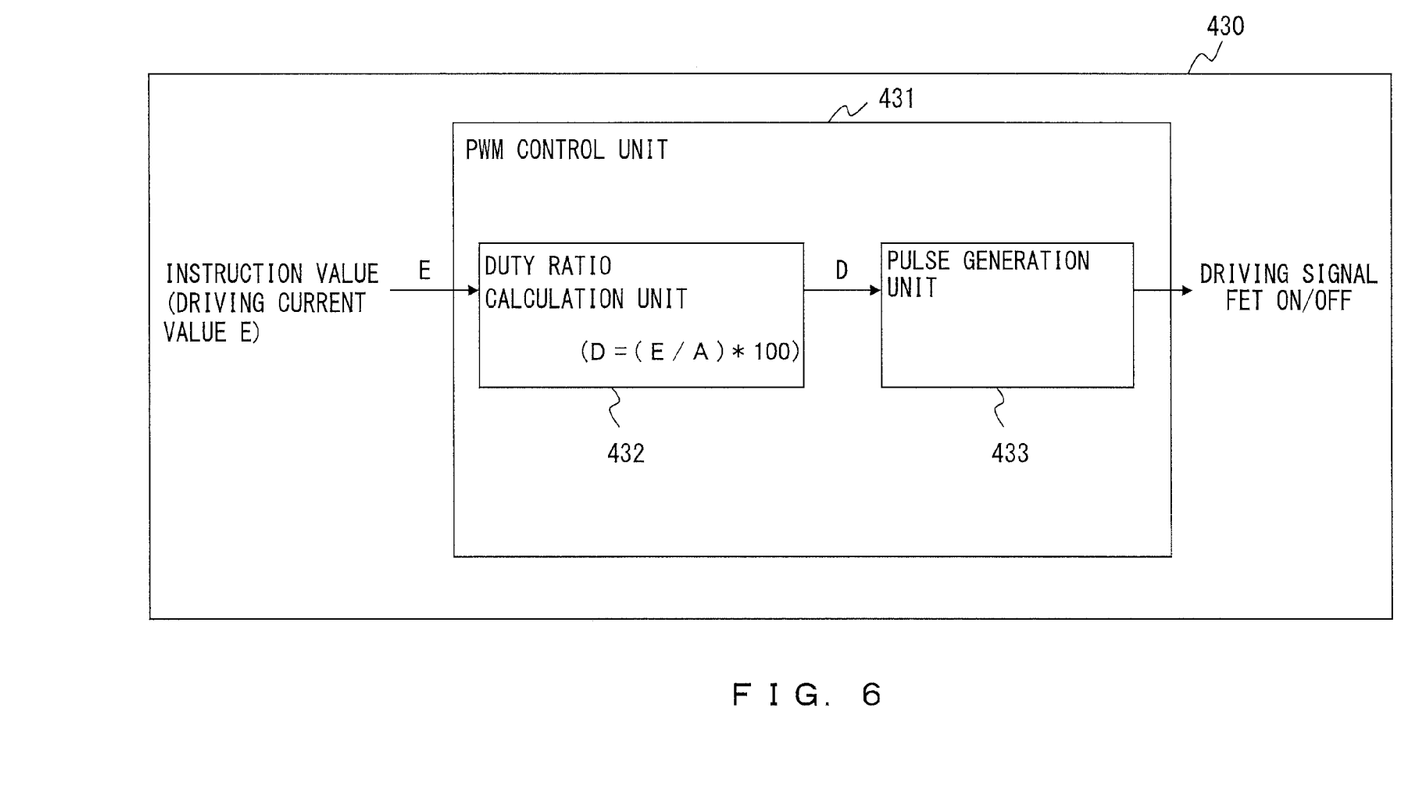
FIG. 6 illustrates a configuration example of part of an FPGA.

Additionally, for example, in the endoscope system 100 including the image pickup apparatus according to each of the embodiments, the position control unit 320 may include a bridge circuit of a constant current type as a VCM driving circuit that outputs a driving signal to the lens driving unit 240. When the bridge circuit of the constant current type is used as the VCM driving circuit in this way, the following advantages are achieved, unlike in a case where a bridge circuit of a constant voltage type is used as the VCM driving circuit. For example, the use of the bridge circuit of the constant current type can prevent the following situation that is possibly caused by using the bridge circuit of the constant voltage type. Namely, this is a situation leading to the possibility that the VCM cannot be accurately controlled as intended and the zoom operation cannot be accurately performed due to fluctuations, caused by the scope length of the endoscope 200, of an electric resistance between the lens driving unit 240 and the position control unit 320, and variations in an electric resistance of an individual VCM itself, which is the lens driving unit 240. Moreover, for example, when the bridge circuit of the constant voltage type is assumed to be used, the VCM needs to be controlled by taking into account the above described fluctuations and variations in the electric resistance, leading to complexity in the control. In contrast, when the bridge circuit of the constant current type is used, the above described fluctuations and variations in the electric resistance do not affect the value of a driving current of the VCM. Therefore, the VCM can be controlled as intended, making it possible to accurately perform the zoom operations. Moreover, a current can be stably supplied to the VCM, thereby eliminating the need for the complex control. When the bridge circuit of the constant current type is used as the VCM driving circuit in this way, the lens driving unit 240 and the position control unit 320 are implemented, for example, with a configuration illustrated in FIG. 4. In FIG. 4, a VCM 410 corresponds to the lens driving unit 240, whereas a VCM driving circuit 420 and an FPGA (Field Programmable Gate Array) 430 correspond to part of the endoscope control unit 300 including the position control unit 320. Here, the VCM driving circuit 420 is implemented, for example, with a circuit configuration illustrated in FIG. 5, and part of the FPGA 430 is implemented, for example, with a configuration illustrated in FIG. 6. The VCM driving circuit 420 is implemented with the bridge circuit of the constant current type that is configured with a bridge circuit of FETs (Field Effect Transistors) in the constant current circuit as illustrated in FIG. 5, and the FPGA 430 performs a PWM (Pulse Width Modulation) control for the VCM driving circuit 420, so that the VCM driving circuit 420 outputs a driving signal to the VCM 410. As illustrated in FIG. 6, the FPGA 430 includes a PWM control unit 431 that performs a PWM control for the VCM driving circuit 420. The PWM control unit 431 outputs an ON/OFF signal to each of the FETs of the VCM driving circuit 420 on the basis of an instruction value. The PWM control unit 431 includes a duty ratio calculation unit 432 and a pulse generation unit 433. The duty ratio calculation unit 432 obtains a pulse duty ratio D by calculating $D=(E/A) \times 100$ with the use of the input instruction value (driving current value) E, and a current value A of the constant current circuit of the VCM driving circuit 420, and outputs the obtained ratio to the pulse generation unit 433. The pulse generation unit 433 outputs an ON/OFF signal to each of the FETs of the VCM driving circuit 420 in accordance with the input pulse duty ratio D. In this way, the calculation of the pulse duty ratio can be simplified in the PWM control unit 431, whereby the usage rate of the PWM control unit 431 in the FPGA 430 can be reduced. Moreover, the PWM control unit 431 performs the PWM control with reference to the current value of the constant current circuit of the VCM driving circuit 420, whereby the PWM control unit 431 can perform the control not affected by the type of the endoscope 200.

The above described embodiments refer to the specific examples of the present invention for ease of understanding of the invention, and the present invention is not limited to the aforementioned embodiments. The present invention can be variously modified and changed within a scope that does not depart from a concept of the invention laid down in the claims.

As described above, according to the present invention, an image pickup apparatus that can accurately control a position of a zoom lens can be provided.

What is claimed is:

1. An image pickup apparatus, comprising:
   an image pickup optics system that forms an optical image of a subject on an imaging surface;
   a variable magnification lens that is part of the image pickup optics system, that is provided to be movable in a direction of an optical axis of the image pickup optics system, and that enlarges or reduces the optical image formed on the imaging surface in association with a movement of the variable magnification lens;
   a position detection unit that detects a position of the variable magnification lens in the direction of the optical axis;
   a storage unit that stores, as output characteristic information about a characteristic of an output of the position detection unit according to a position of the variable magnification lens in the direction of the optical axis, information including a wide-angle-end output value, which is an output value of the position detection unit when the variable magnification lens is made to touch a wide-angle end, a telephoto-end output value, which is an output value of the position detection unit when the variable magnification lens is made to touch a telephoto end, and a slope of a linear line obtained when the characteristic of the output of the position detection unit according to the position of the variable magnification lens in the direction of the optical axis is linearly approximated in each of a plurality of small sections into which a movement section from the wide-angle end to the telephoto end of the variable magnification lens is partitioned; and
   a driving control unit that performs a control for moving the variable magnification lens on the basis of the output characteristic information, wherein
   the driving control unit performs the control for moving the variable magnification lens on the basis of the output characteristic information so that a result of a multiplication between an inverse number of a slope of a linear line corresponding to a small section to which a current position of the variable magnification lens belongs and the amount of an output change of the position detection unit per unit time can become constant.

2. The image pickup apparatus according to claim 1, further comprising an obtainment unit that obtains an output value of the position detection unit, wherein the driving control unit performs the control for moving the variable magnification lens from the wide-angle end to the telephoto end when the image pickup apparatus is powered on, and the obtainment unit obtains a wide-angle-end output value, which is an output value of the position detection unit when the variable magnification lens remains at the wide-angle end, and a telephoto-end output value, which is an output value of the position detection unit when the variable magnification lens remains at the telephoto end.

3. The image pickup apparatus according to claim 2, further comprising a determination unit that determines whether the position detection unit and/or the driving control unit is either normal or abnormal, on the basis of the wide-angle-end output value and the telephoto-end output value that are obtained by the obtainment unit when the image pickup apparatus is powered on and the wide-angle-end output value and the telephoto-end output value that are included in the output characteristic information stored in the storage unit.

* * * * *